(12) United States Patent
Wohlgemuth et al.

(10) Patent No.: US 8,255,047 B1
(45) Date of Patent: Aug. 28, 2012

(54) CARDIAC PACING SYSTEM WITH IMPROVED PHYSIOLOGICAL EVENT CLASSIFICATION AND HEART MONITORING BASED ON DSP

(75) Inventors: Peter W. Wohlgemuth, Neukirchen (DE); Geeske Van Oort, Nieuwleusen (NL); Peter Van Dam, Nijmegen (NL)

(73) Assignee: Medtronic, Inc, Minneapolis, MN (US)

( * ) Notice: Subject to any disclaimer, the term of this patent is extended or adjusted under 35 U.S.C. 154(b) by 0 days.

(21) Appl. No.: 09/399,318

(22) Filed: Sep. 20, 1999

Related U.S. Application Data

(63) Continuation-in-part of application No. 09/158,566, filed on Sep. 22, 1998, now Pat. No. 6,029,087.

(51) Int. Cl.
*A61N 1/37* (2006.01)
(52) U.S. Cl. .............. 607/9; 607/26; 128/901; 600/509
(58) Field of Classification Search ............... 607/9, 14, 607/2, 4, 5, 26, 17, 3; 128/901, 902; 600/509, 600/515, 516–519, 521
See application file for complete search history.

(56) References Cited

U.S. PATENT DOCUMENTS

| | | | |
|---|---|---|---|
| 4,509,529 A * | 4/1985 | Money et al. | |
| 4,742,458 A * | 5/1988 | Nathans et al. | |
| 5,010,887 A * | 4/1991 | Thornander | |
| 5,086,772 A * | 2/1992 | Larnard et al. | |
| 5,271,411 A * | 12/1993 | Ripley et al. | |
| 5,351,696 A * | 10/1994 | Riff et al. | |
| 5,381,803 A * | 1/1995 | Herleikson et al. | 607/5 |
| 5,388,586 A * | 2/1995 | Lee et al. | |
| 5,427,112 A * | 6/1995 | Noren et al. | |
| 5,511,553 A | 4/1996 | Segalowitz | 128/696 |
| 5,555,888 A | 9/1996 | Brewer et al. | 128/702 |
| 5,694,943 A | 12/1997 | Brewer et al. | 128/702 |
| 5,782,887 A * | 7/1998 | van Krieken et al. | 607/25 |
| 5,891,171 A * | 4/1999 | Wickham | 607/4 |

* cited by examiner

*Primary Examiner* — Kennedy Schaetzle
(74) *Attorney, Agent, or Firm* — Thomas F. Woods; Eric R. Waldkoetter; Tom G. Berry

(57) ABSTRACT

There is provided an implantable cardiac pacing system or other cardiac monitoring system having an enhanced capability to classify intracardiac signals through a combination of DSP techniques and software algorithms. The implantable device has one or more DSP channels corresponding to different signals which are being monitored. Each DSP channel most preferably amplifies the incoming signal, converts the signal from analog to digital form, digitally filters the converted signals to provide a filtered signal, operates on the filtered signal to provide a slope signal, determines from the filtered and slope signals when an intracardiac event has been detected, signal processes the filtered and slope signals for a predetermined analysis interval after threshold crossing, and generates a plurality of wave parameters corresponding to the signal. The generated wave parameters are further operated on by a programmable algorithm to classify the detected event based upon DSP-generated parameters, and then monitor or detect the onset, development or presence of an undesired heart condition in a patient. The system may further provide for the delivery of treatment, storage of intracardiac data, or provision of a warning to a patient or physician in response to the detection of such a heart condition.

34 Claims, 16 Drawing Sheets

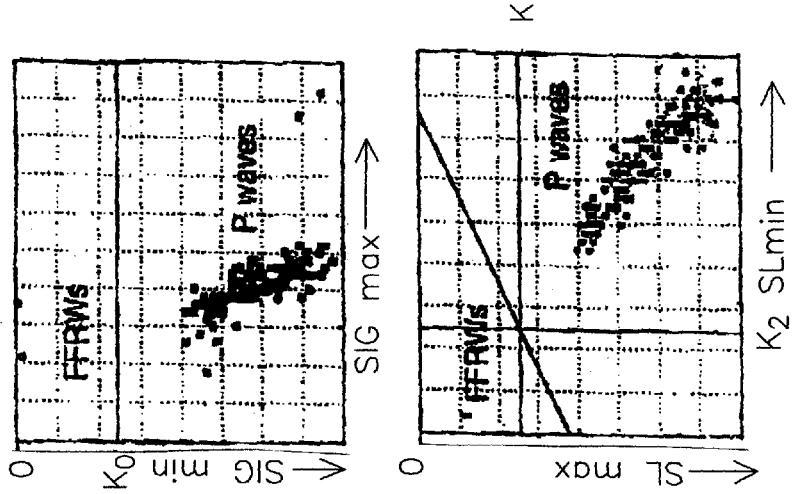
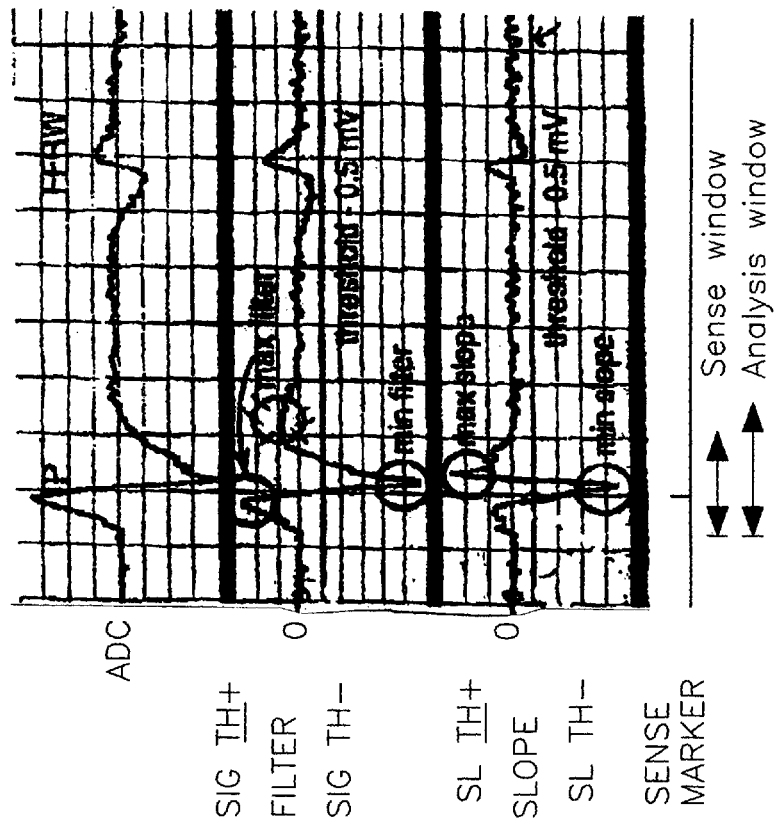

CARDIAC PACING SYSTEM WITH IMPROVED PHYSIOLOGICAL EVENT CLASSIFICATION AND HEART MONITORING BASED ON DSP

This application is a continuation-in-part of U.S. application Ser. No. 09/158,566 filed Sep. 22, 1998, entitled "Cardiac Pacing System with Improved Physiological Event Classification based on DSP" to Peter Wohlgemuth, now U.S. Pat. No. 6,029,087 the disclosure of which is hereby incorporated by reference herein in its entirety.

FIELD OF THE INVENTION

The present invention relates to cardiac pacing systems having the capability to recognize and classify sensed cardiac signals, where recognition and classification is based upon characteristics of the sensed signal. The present invention also relates to systems, which utilize digital signal processing for analysis of sensed signals in combination with a software-based decision algorithm.

BACKGROUND OF THE INVENTION

Implantable cardiac pacemakers need to accurately process sensed signal information to determine when a genuine cardiac signal has in fact been sensed, and then and to accurately identify, or classify the signal. Separating cardiac signals from polarization effects and other noise artifacts has always been a substantial problem, and a great deal of effort has been placed on improving input circuits for this purpose. Additionally, it is often important to classify a sensed or acquired signal to determine whether the signal is, for example, a P-wave, a Far Field R-wave (FFRW), or an evoked response R wave. Many prior art techniques have been developed for signal classification, but improvement is still needed. For example, one prior art technique is to establish a variable timing window, and classify the event in terms of the timing of the signal received during window. However, early beats, ectopic signals, etc. can fool such a technique, and noise can still mask the signal, which is sensed within window. Other known techniques include morphology analysis, comparisons in the time and frequency domain, etc. While many of these techniques provide reasonably good results, they can involve considerable circuit complexity and frequently do not eliminate the probability of error due to detection of noise or other artifacts.

The advent of digital signal processing (DSP) has provided a tool, which can be very useful in the environment of an implanted medical device, e.g., an implanted pacemaker. In DSP technology, the incoming sense signal is converted to a digital signal, e.g., an 8 bit signal at some sample rate. Successive digital signals can be processed with high reliability, in a manner, which is essentially hardware-controlled by the DSP circuitry. More recently, DSP technology has advanced so as to provide the possibility of a low current chip, which can be used in an implantable pacemaker to provide significant sensed signal processing capability.

The utilization of a DSP chip for an implantable pacemaker makes available an enhanced capability of processing sensed signals, so as to enable more accurate classification of the signal. Such DSP processing, together with a microprocessor and an appropriate signal classification algorithm, provides a powerful tool for accurately sensing and classifying intracardiac signals. In addition to this combined hardware and software capability, there is a need to provide an optimum decision algorithm for using the DSP-generated signal parameters so as to accurately and reliably classify sensed intracardiac signals.

Furthermore, DSP-generated signal parameters can also be employed to assess and monitor the state of the heart and detect changes such as the onset or presence of ischemia, heart failure, and other heart diseases. See, for example, U.S. Pat. No. 5,511,553 entitled "Device-System and Method for Monitoring Multiple Physiological Parameters Continuously and Simultaneously" to Segalowitz, U.S. Pat. No. 5,694,943 entitled "Method and Apparatus for Automatic, Adaptive, Active Facilitation to Access Myocardial Electrical Instability" to Brewer et al., and U.S. Pat. No. 5,555,888 entitled "Method and Apparatus for Automatic, Adaptive, Active Facilitation to Access Myocardial Electrical Instability", also to Brewer et al.

SUMMARY OF THE INVENTION

It is an object of this invention to provide an implantable pacemaker having combined DSP-microprocessor capability for reliably processing and classifying intracardiac signals so as to provide the pacemaker with reliable cardiac event data. It is a further object to utilize an optimum combination of DSP processing for generating signal parameters, and software for analyzing the DSP-generated signal parameters so as to make reliable signal classifications.

In accordance with these objectives, there is provided an implantable pacemaker system, having a pacemaker and lead, the lead serving to deliver generated pacing pulses to the patient's heart and to pick up and deliver sensed intracardiac signals to the pacemaker. The pacemaker has DSP circuitry, preferably provided on a DSP chip, for receiving the sensed cardiac signals, digitizing them, and obtaining for each sensed signal a predetermined set of parameters from which a signal classification is made. The signal parameters are passed to a microprocessor, which contains a classification algorithm for analyzing the parameters and making a classification decision.

In a preferred embodiment, the DSP circuitry determines up to nine parameters for each analyzed signal, each parameter representing a predetermined characteristic of the signal. The DSP circuitry continuously filters the incoming signals and generates the slew rate, or slope of the signal from the filtered signal; and it compares each of the filtered and slope signals to a respective predetermined positive and negative threshold. A sense window of a predetermined time limit, e.g., 50 ms, is started with the first threshold crossing, and a signal is deemed to be sensed only when it has crossed one filtered signal threshold and one slope threshold within the sense window. Whenever a striking signal appears, the DSP logic times out an analysis window of predetermined duration, e.g., 70 ms. The analysis window may be initiated at the time of the first threshold crossing; at the time of a "sense"; or at a software-generated time produced under control of the processor. For each of the filtered signal and the slope signals, a maximum and minimum value is obtained during the analysis window, and a time interval from signal sense to the maximum and minimum for each of these signals is obtained. Additionally, a signal window length from the first crossing of any one of the four thresholds to the last such crossing during the analysis window is generated, providing a ninth parameter.

A separate DSP channel is used for sensing each respective type of signal, and for generating parameters corresponding to such signal. The parameters from each channel are transferred on a data bus to a microprocessor, which is software controlled to classify each sensed signal as a function of two or more of the DSP-generated parameters. The software includes a classification algorithm for each DSP channel, and each algorithm is programmable so that classification for the patient can be optimized for each signal type.

It is a still further object of the present invention to store within an electronic memory of an implantable medical device the wave parameters generated by the one or more DSPs of the present invention so that changes occurring over time respecting the characteristics of wave parameters relating to a certain type of signal or wave may be detected and, if appropriate, acted upon by, for example, triggering the capture of diagnostic data, warning or alerting a patient or a physician of the onset or development of an undesired heart condition, delivering an appropriate intracardiac cardioversion, pacing or defibrillation therapy, or delivering an appropriate drug or gene therapy.

BRIEF DESCRIPTION OF THE DRAWINGS

FIG. 5A is a series of curves showing an atrial signal as converted into digital form; the filtered signal; the slope of the filtered signal; and markers indicating when a signal is sensed and the end of the analysis window; FIG. 5B is a plot of the minimum and maximum values of the filtered signal for a number of signals obtained from an atrial channel; FIG. 5C is a plot of the minimum and maximum values of the slope signal for the same signals as illustrated in FIG. 5B.

DETAILED DESCRIPTION OF THE PREFERRED EMBODIMENTS

Figure 1:
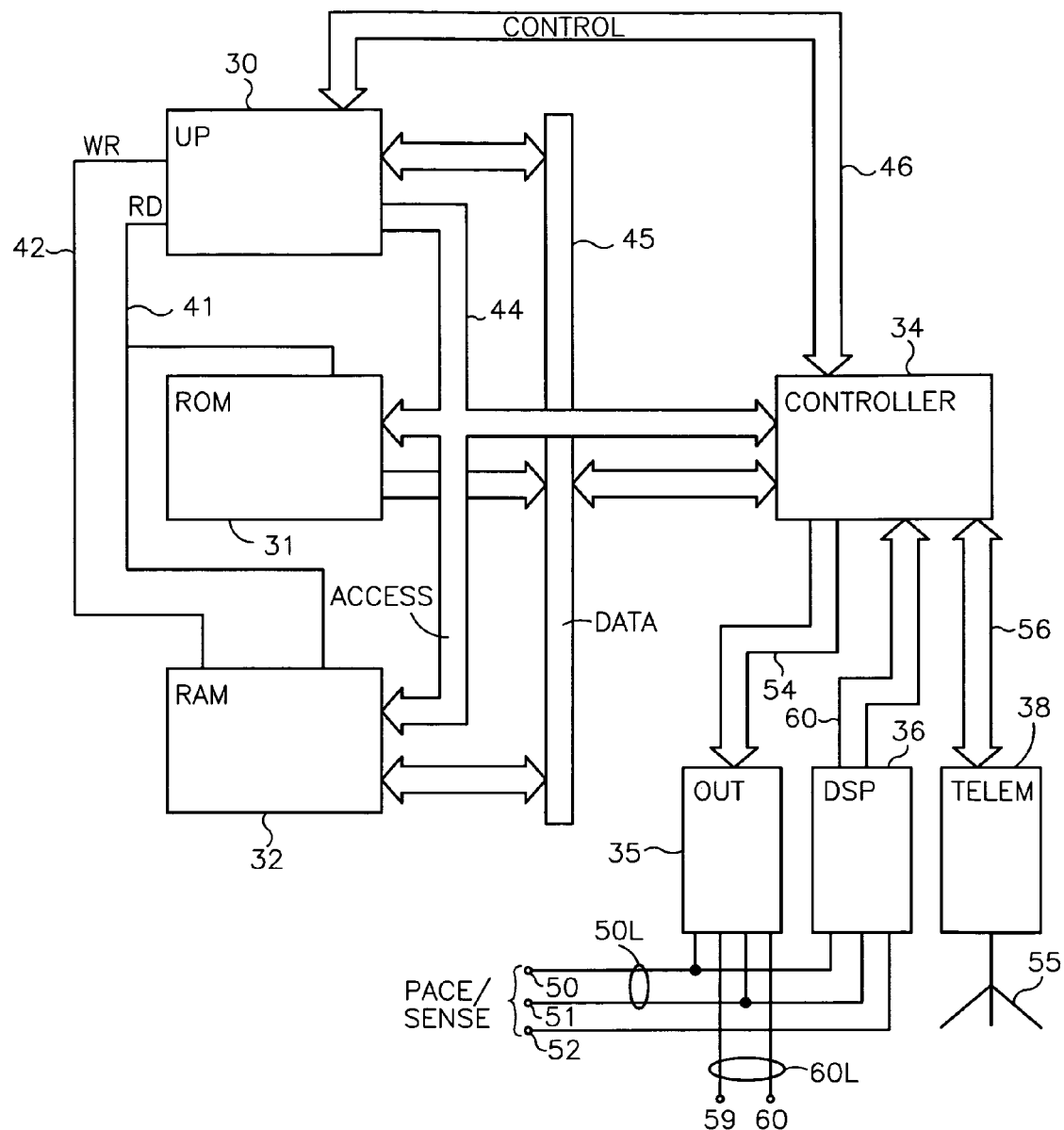
FIG. 1 is a block diagram showing the primary components of an implantable pacemaker in accordance with this invention, illustrating the position of a DSP chip and a microprocessor in the overall scheme of sensed signal processing.

Referring now to FIG. 1, there is shown a functional block diagram of an implantable pacemaker of a type with which the present invention may be practiced. It is to be noted that FIG. 1 is representative of such a pacemaker, and is not limiting in the actual architecture of the pacemaker. It is presented for the purpose of discussing data flow and, in particular, the position of a DSP chip and a microprocessor for purposes of sensing, analyzing and classifying sensed intracardiac signals. Accordingly, FIG. 1 is considered to be exemplary rather than limiting with regard to the present invention. While the invention is disclosed as embodied in a pacemaker, it is likewise applicable to incorporation in a cardioverter, or combined cardioverter pacemaker, cardioverter defibrillator pacemaker, etc. Further, while the discussion of FIG. 1 assumes a single chamber ventricular pacing system, it is to be understood that the invention is applicable to dual chamber and multi-chamber systems, e.g., in a preferred dual chamber embodiment, the DSP chip has three channels, for respective processing of P, R and T wave signals.

The primary elements of the apparatus illustrated in FIG. 1 are microprocessor 30, read only memory 102, random access memory 32, a digital controller 34, output amplifier 35, DSP circuitry 36, and a telemetry/programming unit 38. Read only memory 31 stores the basic programming for the device, including the primary instructions set defining the computations performed to derive the various timing intervals performed by the device. Random access memory 32 serves to store the values of variable control parameters, such as programmed pacing rate, pulse widths, pulse amplitudes, and so forth, which are programmed into the device by the physician. Reading from random access memory 32 and read only memory 31 is controlled by RD-line 41. Writing to random access memory 32 is controlled by WR-Line 42. In response to a signal on RD-Line 41, the contents of random access memory 32 or read only memory 31 designated by the then present information on address bus 44 are placed on data bus 45. Similarly, in response to a signal on WR-line 41, information on data bus 45 is written into random access memory 32 at the address specified by the information on address bus 44.

Controller 34 performs all of the basic timing and control functions of the illustrative pacemaker device. Controller 34 includes at least one programmable timing counter, e.g., initiated on paced or sensed ventricular contractions, for timing out intervals thereafter. This timing counter is used to define the escape intervals for timing generation of pace pulses, as well as for timing the respective durations of the charge and recharge pulse portions of triphasic pulses. Controller 34 triggers output pulses to be generated and delivered from output stage 35, and it generates interrupts on control bus 46 for cyclically waking microprocessor 30 from its sleep state to allow it to perform the required functions. For a single chamber pacemaker output circuit 35 is coupled to electrodes 50 and 51 which are employed both for delivery of pacing pulses and for sensing of cardiac signals. Electrode 50 is typically located on the distal tip end of an endocardial lead 50L, and for ventricular pacing is preferably placed in the apex of the right ventricle; for atrial pacing, of course, it is placed in the patient's atrium. Electrode 51 is preferably a ring electrode, as used with a bipolar lead. Electrode 52 represents the pacemaker housing, which may be used as the indifferent electrode for selected unipolar pacing and/or sensing operations. Of course, for a dual or multi-chamber pacing system, additional electrodes are employed. For example, electrodes 59,60 carried by lead 60L may be used for pacing and sensing in the atrium, while electrodes 50,51 are used in the ventricle. Output circuit 35 is controlled by controller 34 through bus 54 to determine the amplitude and pulse width of the pulse to be delivered and to determine which electrode pair is to be employed to deliver the pulse.

Cardiac signals are sensed at a desired pair or pairs of electrodes; bipolar and/or unipolar sensing may be used. For "combipolar" sensing, a unipolar lead in the atrium and a unipolar lead in the ventricle are used, e.g., the signals are picked up at electrodes 50,59. Sense signals are inputted to DSP block 36, which comprises a number of signal processing channels corresponding to signals of interest. For example, in a dual chamber pacemaker which incorporates P wave processing either for rate control, capture detection or any other reason, there are three channels for respective signal processing of the P, R and T waves. The data resulting from the digital signal processing is transmitted via bus 60 through controller 34 and bus 46 to microprocessor 30, for the signal classification operations, as well as any other necessary calculations.

External control of the implanted device is accomplished via telemetry/control block 38, which allows communication between the implanted device and an external programmer (not shown). Radio communication is typically employed via antenna 55. Appropriate telemetry/programming systems are well known in the art; the present invention is workable with any conventional telemetry/programming circuitry. Information entering the pacemaker from the programmer is passed to controller 34 via bus 56. Similarly, information from the pacemaker is provided to the telemetry block 38 via bus 56, for transmission to the external programmer. Of importance to this invention, the classification algorithms for processing the parameters generated by each DSP channel can be reprogrammed in a known manner.

Figure 2A:
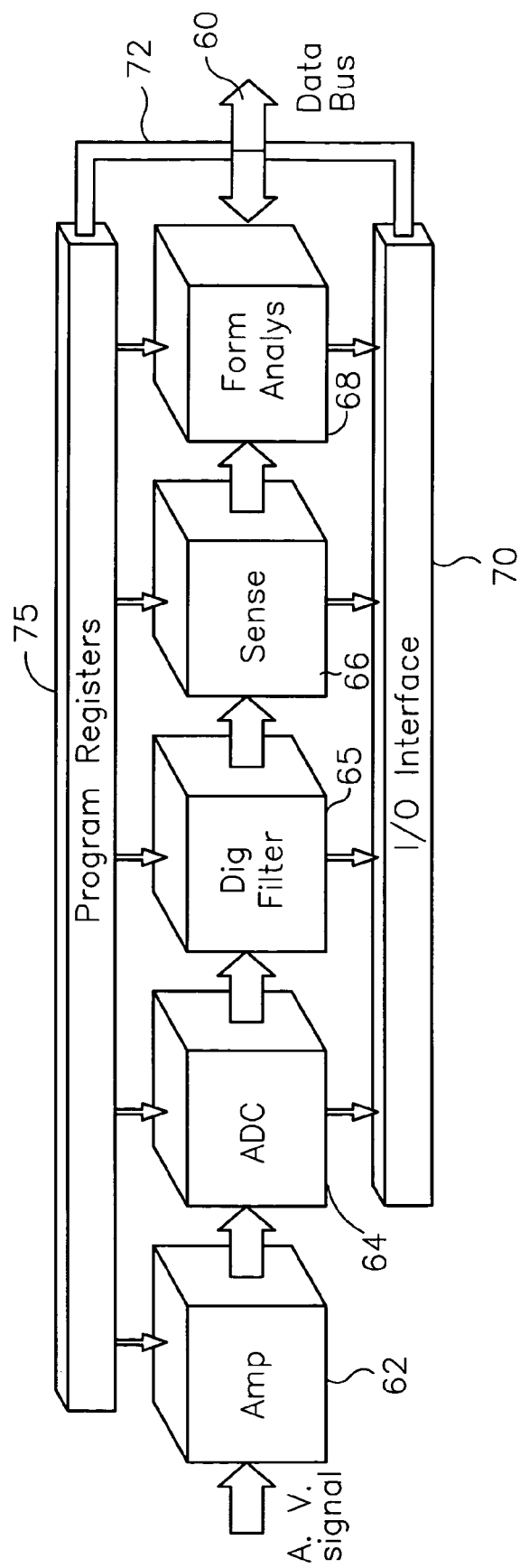
FIG. 2A is a block diagram illustrating the primary functional and structural components of a DSP channel in accordance with this invention.
Figure 2B:
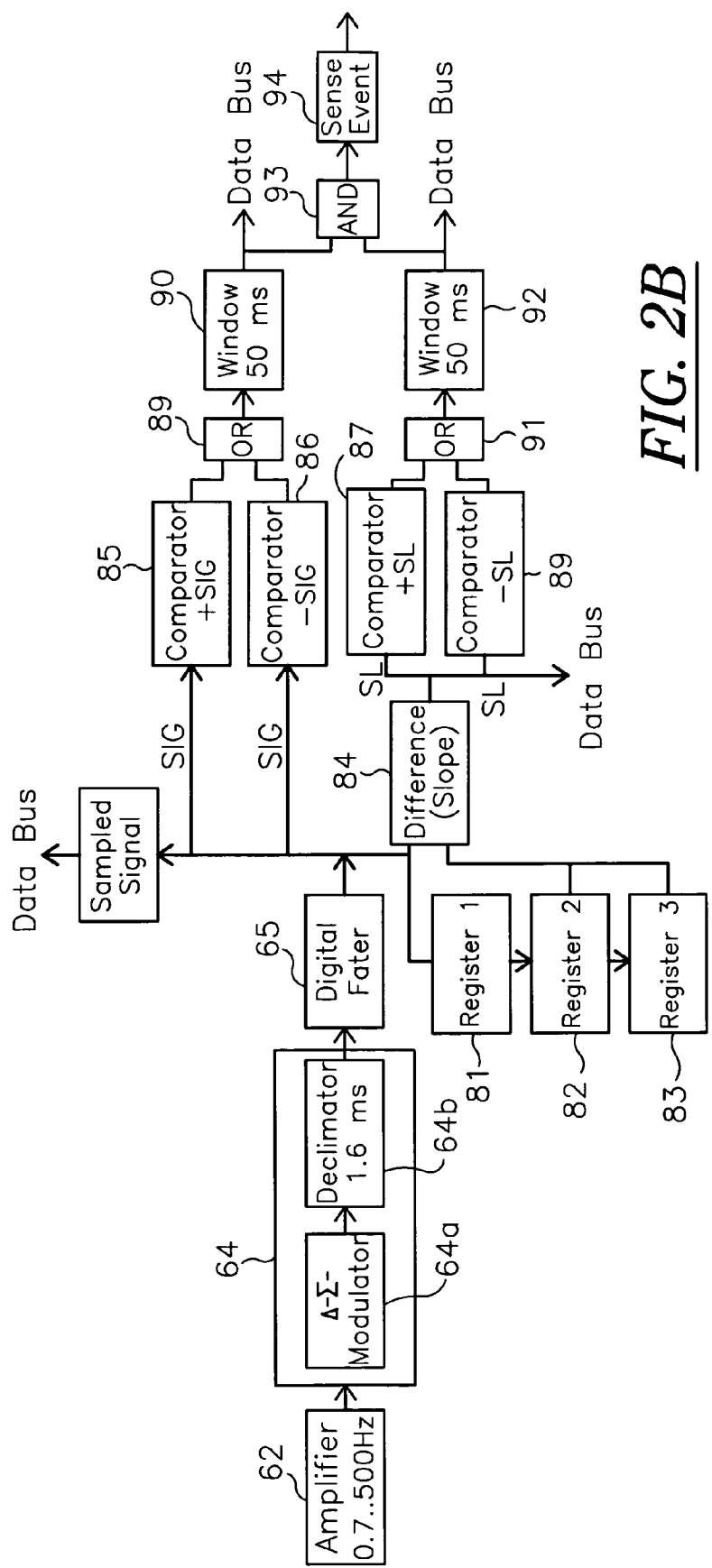
FIG. 2B is a block diagram showing the DSP components for generating a sense signal.
Figure 3A:
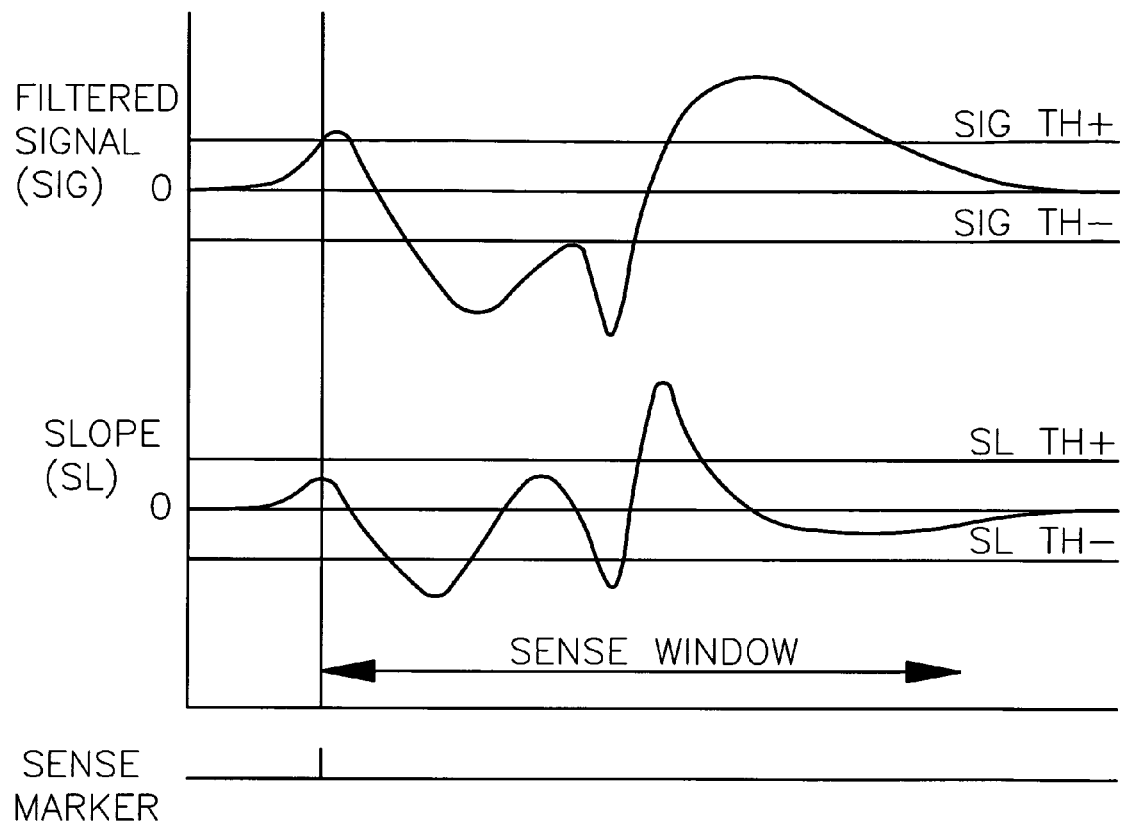
FIG. 3A is a set of curves illustrating a sampled and filtered cardiac signal, a slope signal derived from the filtered signal, and the determination of a sense window and sense marker.

Referring now to FIG. 2A, there is shown a diagram representing the primary components of a DSP chip 36. The chip is manufactured with a chip area of about 20 mm$^2$, and draws about 0.7-1.5 microamps per channel. FIG. 2A shows an atrial (A) or ventricular (V) signal introduced into a DSP channel; it is to be understood that as many similar channels as desired are provided for signal processing of respective signals. The signal, still in analog form, is first passed through an amplifier 62, having a filter characteristic of about 0.7 to 500 Hz. The amplified analog signal is passed into A/D converter 64, for generation of a digital signal. The A/D conversion is suitably done by a delta-sigma modulator, as shown in FIG. 2B, followed by a decimater to provide typically 8-bit bytes at 1.6 ms intervals. The digital signal from block 64 is connected to digital filter 65 which is suitably a digital bandpass filter having a characteristic to eliminate low frequency signal components and the offset of the converter, as well as to take out high frequency artifacts. The output of block 65, referred to as SIG in FIG. 3A, is connected to sense block 66. Sense block 66 obtains the slew rate, or slope of the signal, also hereafter referred to as the SL signal, and then compares both the SIG and SL signals to plus and minus threshold voltages to derive a "sense" signal.

As seen in more detail in FIG. 2B, the output of digital filter 65, in one embodiment, is connected to a series of three registers, Registers 81, 82 and 83 being cascaded so that at each sample the digital signal in Register 1 is passed to Register 2, and the signal in Register 2 is passed to Register 3. The difference is then obtained at difference circuit 84, by taking the difference between either Register 1—which holds the SIG signal—and Register 2; or the difference between Register 1 and Register 3. At block 85 the SIG signal is compared with a positive voltage threshold, and at block 86 the SIG signal is compared with a negative threshold signal. Whenever the SIG exceeds either threshold, an output is passed through OR gate 89, and triggers generation of a window signal of 50 ms duration, shown at block 90. Likewise, the difference or SL signal from block 84 is compared at 87 with a positive threshold and at 88 with a minus threshold, and if either threshold is exceeded, a signal is passed through OR gate 91 to window circuit 92. Whenever there is a first signal through either OR gate 89 or OR date 91, and there follows a signal through the other OR gate within 50 ms, AND circuit 93 produces an output, which is recognized at 94 as a sensed event.

Referring now to FIG. 3A, the upper curve represents the filtered signal (SIG), and the lower signal represents a corresponding slope (SL) signal corresponding to an event which is to be sensed and classified. For each signal, plus and minus threshold values are indicated, i.e., SIG TH+, SIG TH−, SL TH+, and SL TH−. It is seen that in this example, the SIG signal crosses the positive threshold first, and one or tow samples later the SL signal crosses its negative threshold. The 50 ms sense window is illustrated as being timed out from the instant of the first threshold crossing. The identification of a sense event by a sense marker is represented on the bottom line, corresponding to the time when both signals had crossed one of their thresholds.

Figure 2C:
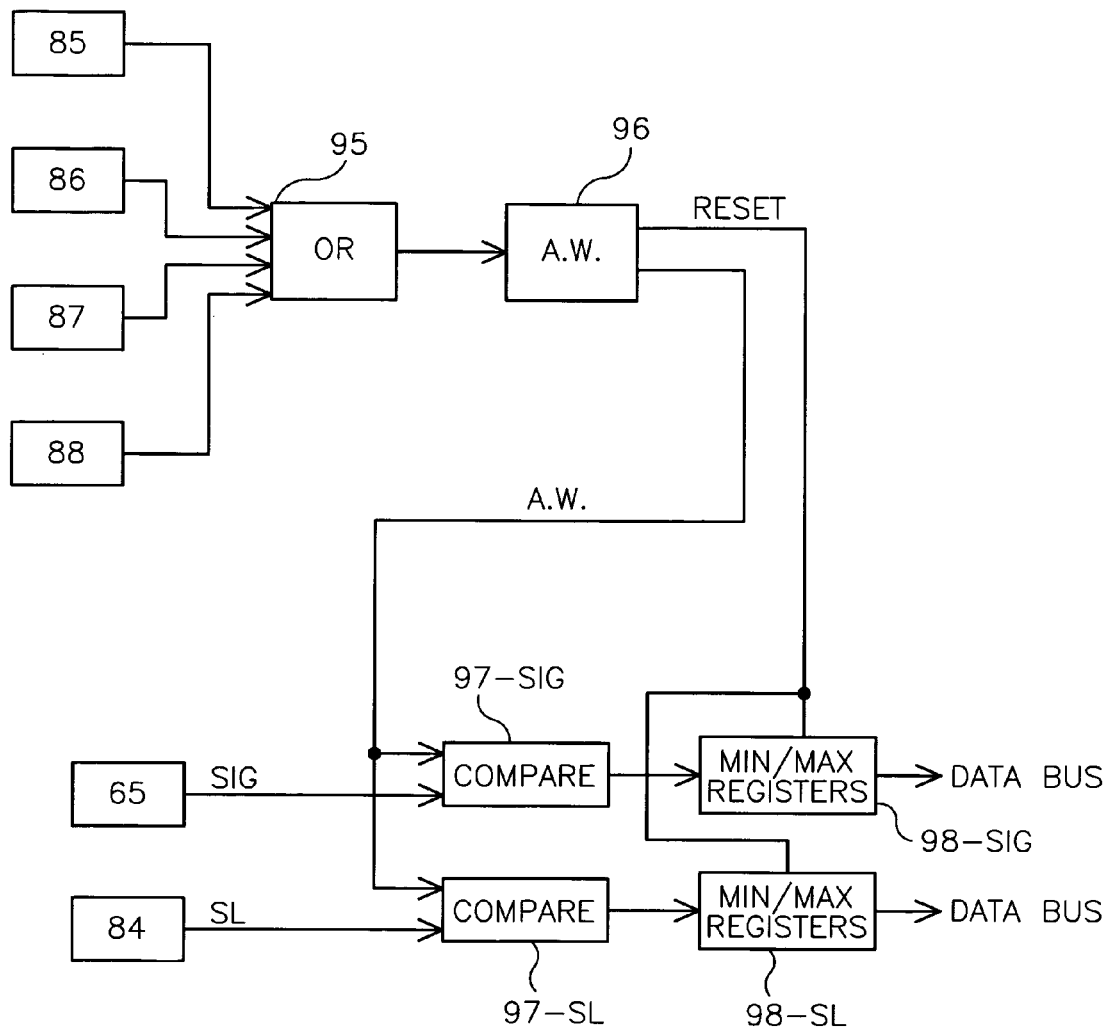
FIG. 2C is a block diagram showing the DSP components for collecting the analysis data.
Figure 3B:
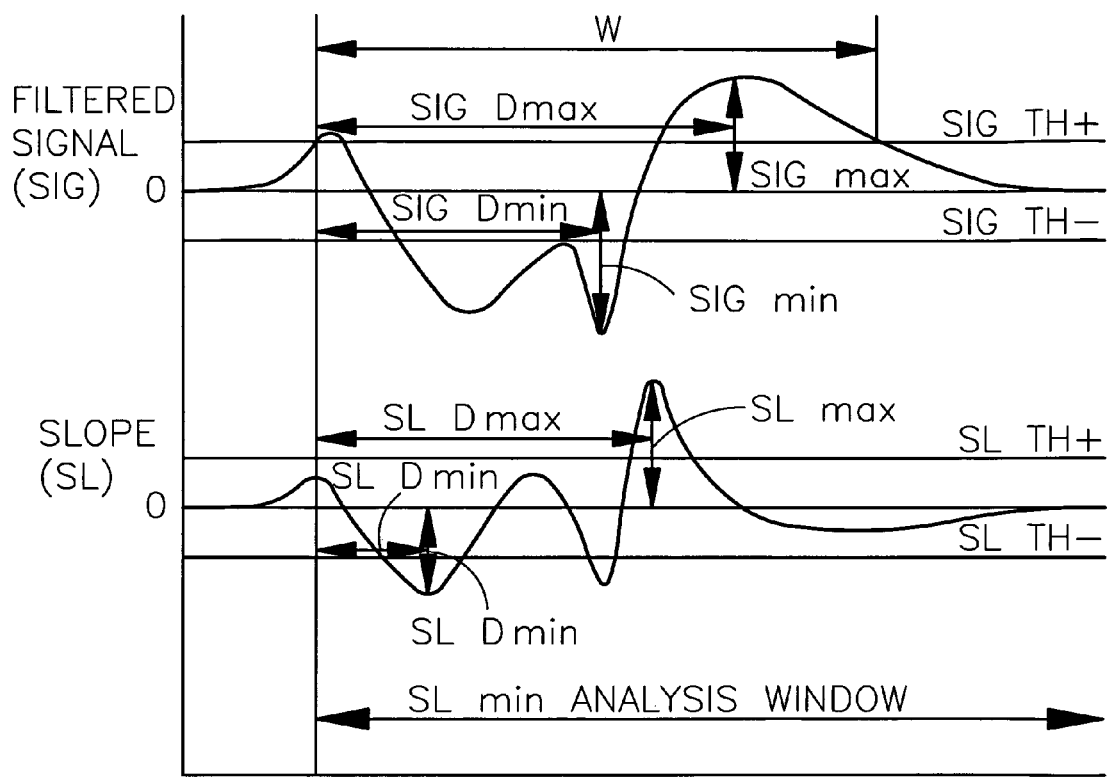
FIG. 3B is a similar set of curves, illustrating the analysis window and the parameters that are obtained for classification of the event.

Referring now to FIG. 2C, there is shown a block diagram of an illustrative circuit corresponding to block 68 of FIG. 2A, titled "form analys". This block is where the DSP circuitry operates during the 70 ms analysis window to extract parameters from the signal under examination, which parameters are shown in FIG. 3B. When the analysis window is active, the SIG and SL values are operated on to obtain the signal parameters that are illustrated in FIG. 3B. Referring first to the filtered signal as illustrated in FIG. 3B, both maximum and minimum values of SIG during the analysis window are obtained; the positive value is indicated as SIGmax and the negative value is indicated as SIGmin. The time from sense to SIGmax is indicated as SIG Dmax (or a delay time corresponding to a maximum value of the signal); and the time from sense to SIGmin is indicated as SIG Dmin (or a delay time corresponding to a minimum value of the signal). Likewise, referring to the SL curve, values of SLmax and SLmin are determined, and the time from sense to each is found, namely SL Dmax and SL Dmin. Additionally, the time from first crossing of a threshold to the last crossing of a threshold is determined as labelled W; in this example W is from the first SIG crossing of the positive threshold to the last SIG crossing of the SIG positive threshold. The parameter "W" may be considered as providing a measure of the "width" of the evaluated signal.

Referring again to the illustrated circuit of FIG. 2C, the analysis window is initiated by the first occurrence of the event signal crossing one of the four thresholds. Thus, the inputs from comparators 85-88, as seen in FIG. 2B, are gated through OR circuit 95, and the first signal gated through initiates the generation of a window signal at circuit 96. The analysis window signal is connected to enable compare circuits 97-SIG and 97-SL. Circuit 97-SIG compares the SIG signal from block 65 with the current values of MIN/MAX registers 98-SIG; and circuit 97-SL compares the SL signal from block 84 with the current values of MIN/MAX registers 98-SL.

The 8-register set, 98-SIG and 98-SL is reset at the start of the analysis window. At each signal sample, the SIG and SL signal samples are separately compared to four respective registers, which correspond to that signal's four respective parameters as seen in FIG. 3B; and new parameter values are written into the corresponding registers. Thus, If SIG<SIG min, then SIG→SIG min, and D→SIG D min;
If SIG>SIG max, then SIG→SIG max, and D→SIG D max;
If SL<SL min, then SL→SL min, and D→SL D min;
If SL>SL max, then SL→SL max, and D→SL D max.

Also, W is recorded as the time from the first crossing of a threshold to the last threshold crossing.

Thus, the parameters are obtained by the DSP circuitry form by continuous operation on each byte of data from the time of the first threshold crossing until the end of the analysis window. The parameters are provided on data bus 60, which is communicated directly through onto bus 46 to microprocessor 30. Note that the output of each of blocks 64, 65, 66 and 68 is connected through I/O interface 70 to a bus 72, which can either connect to data bus 60 or to program registers 75. The registers connect to blocks 62, 64, 64, 66 and 68, and serve a variety of purposes, such as programming amplifier sensitivity, programming threshold levels of the sense block, etc.

Figure 4:
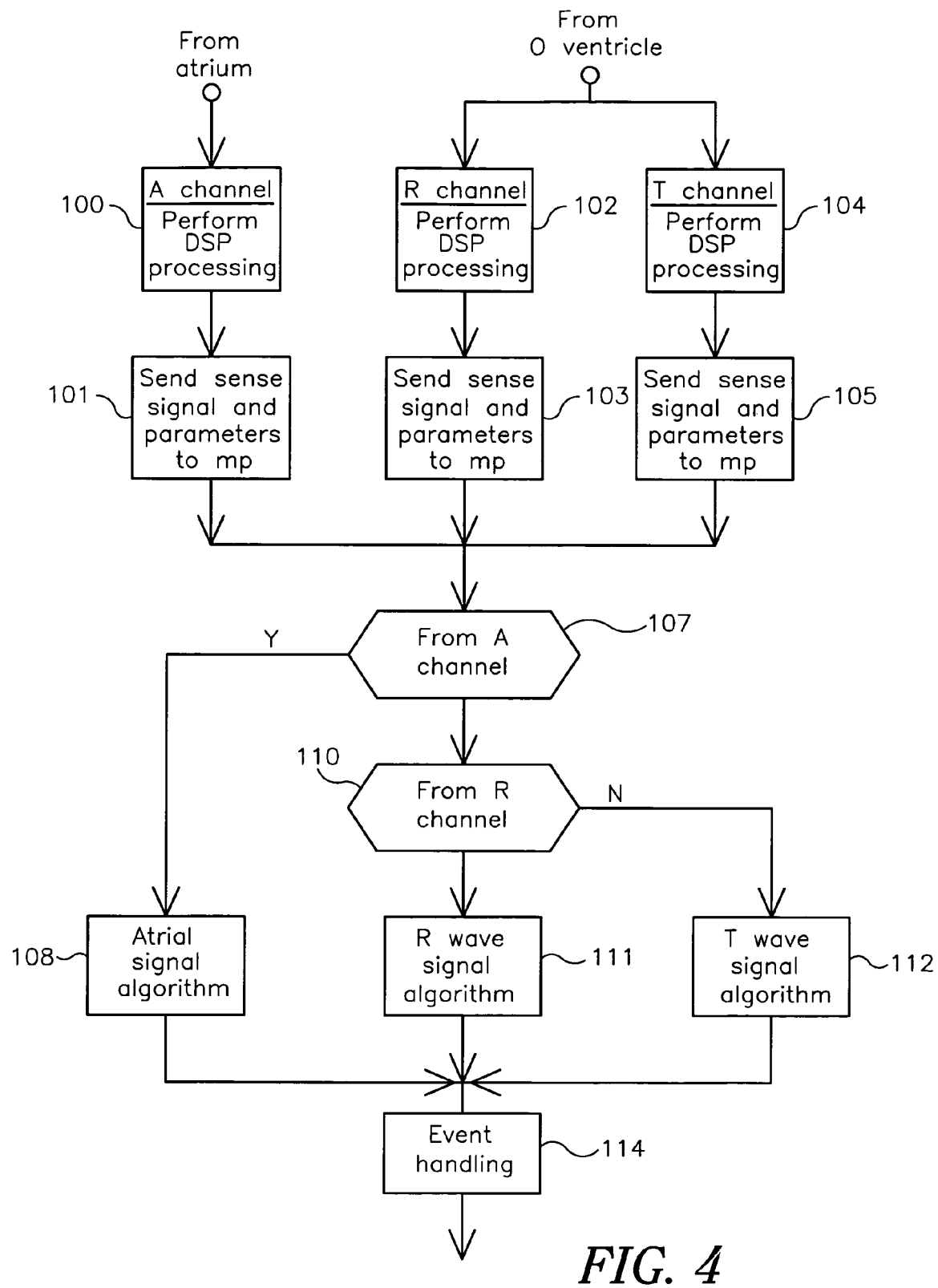
FIG. 4 is a simplified flow diagram showing plural channels of the DSP chip, each operating in combination with a respective signal classification algorithm, and illustrating the primary steps in sensing, classifying and utilizing intracardiac signals in accordance with this invention.

Referring now to FIG. 4, there is presented a flow diagram which gives an overall perspective on the processing operations carried out in a pacemaker system in accord with this invention. As illustrated at block 100, an incoming analog signal which has been sensed in the atrium is inputted to the A channel of the DSP chip. The A channel is programmed with thresholds corresponding to signals sensed in the atrium. The received signal is operated on as discussed above, namely it is amplified; converted from A to D; digitally filtered; the slope signal is obtained; a sense signal is obtained if a signal is in fact present; and the form analysis is performed to obtain the parameters, e.g., up to nine parameters, as set forth above. Following these DSP operations, a sense signal and the parameters are sent to the microprocessor 30, as indicated at block 101. If the signal has come from the ventricle, it is connected to the R channel (102) of the DSP chip and also to the T channel (104). The R channel is programmed with thresholds appropriate to R waves, and performs the same DSP functions as the A channel; the resulting sense signal and parameters are sent to the microprocessor, as shown at block 103. The T channel is programmed with thresholds corresponding to T waves, and likewise performs the functions as shown in FIG. 2A, and thereafter sends data to the microprocessor as shown at 105. The microprocessor determines the channel from which the data has been sent, at 107 and 110, and selects the corresponding algorithm for signal classification. For a signal from the A channel, the data is operated on with an atrial signal algorithm, shown at 108; for a signal from the R channel, the data is operated on with an R wave signal algorithm 111; and for a signal from the T channel, the signal is operated on by T wave algorithm 112. Following a signal classification from any one of the channels, the microprocessor goes on to the appropriate event handling at 114, i.e., predetermined logical steps follow the detection of each respective type of signal. See, for example, U.S. Pat. No. 5,782,887, issued Jul. 21, 1998, incorporated herein by reference, which provides examples of V sense, A sense and T wave event handling.

It is important to note that each microprocessor classification algorithm is programmable. For a given channel which is to process atrial or ventricular signals, any combination of the nine parameters can be utilized, and they are weighted relative to each other. Thus, there is provided a flexibility, wherein the DSP chip very efficiently, obtains the signal parameter data, while the software algorithm for each respective channel is optimally programmed to carry out the calculations for determining signal classification.

Figure 5D:
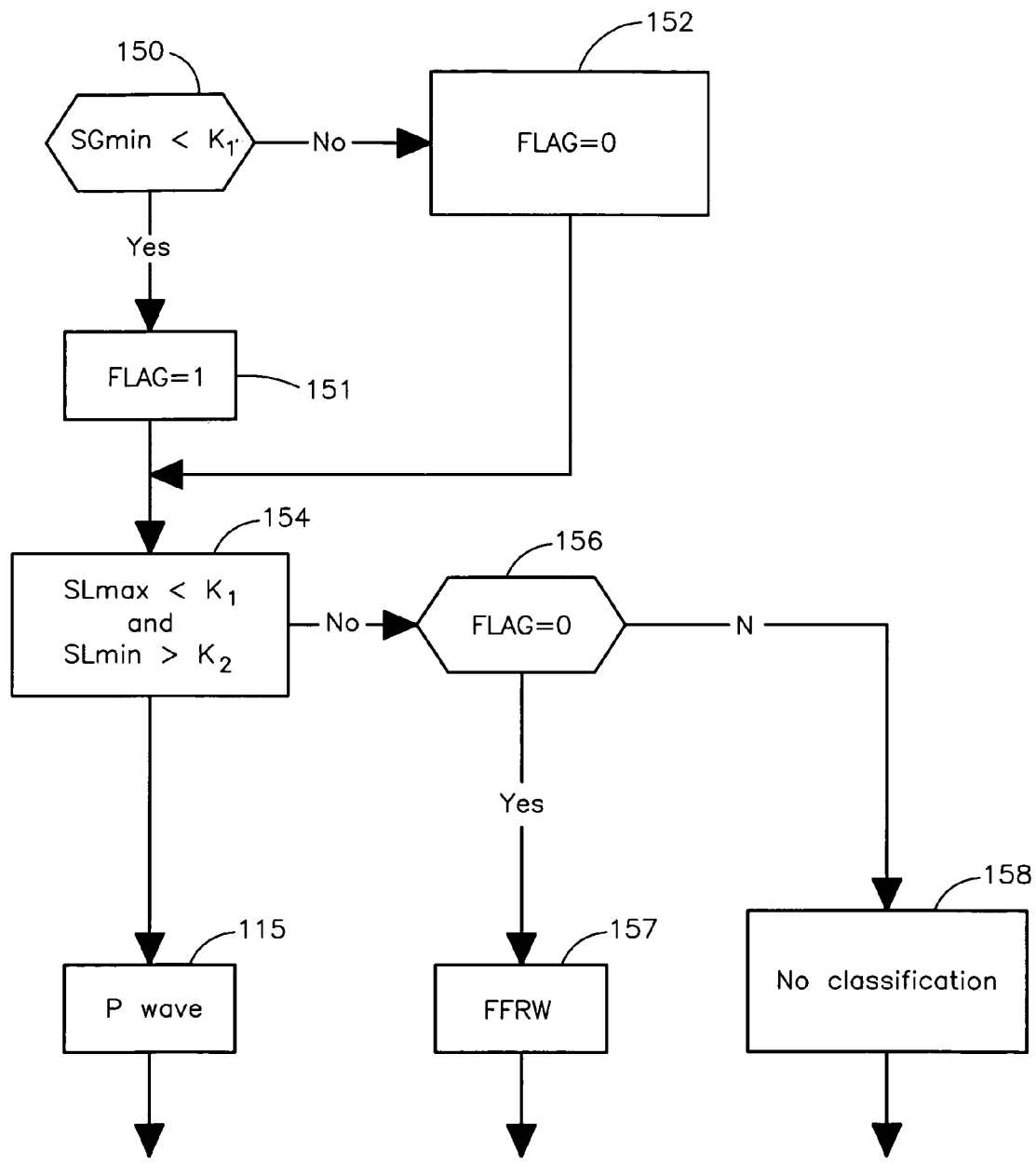
FIG. 5D is a flow diagram illustrating an algorithm for distinguishing between P waves and FFRWs, as used in operating on the parameter data illustrated in FIGS. 5B and 5C.

Referring now to FIGS. 5A-5D, there is illustrated the operation of a channel of the DSP circuitry 36, e.g., A channel 100 as shown in FIG. 4, in providing parameters of an atrial signal in order to distinguish FFRWs from P waves. FIG. 5A presents a series of curves. The top curve represents an unipolar digitized atrial signal, showing P wave and FFRW portions. The second curve represents the filter output, or SIG signal, relative to a negative threshold of 0.5 mV and a positive threshold of 0.5 mv; and illustrates minimum and maximum amplitude points. The third curve is the derived slope (SL) curve, with an indication of a negative threshold of 0.5 mV and a positive threshold of 0.5 my. At the bottom the sense signal, the 50 ms sense window and 70 ms analysis window are indicated.

FIG. 5B is a plot of SIGmin and SIGmax signals, for a plurality of processed signals. It is seen from this that most of the signals have a SIGmin value which is below a predetermined horizontal line, i.e., below a predetermined value of SIGmin shown as $K_0$. In FIG. 5C, data from the same signals is plotted, comparing SLmax with SLmin. In this case, it is seen that P waves fall below a horizontal line shown as $K_1$, and to the right of vertical line $K_2$. That is, signals meeting these criteria have a characteristic of P waves, whereas signals that do not have a characteristic of FFRWs. By satisfying the criteria set forth by FIGS. 5B and 5C, P waves can be distinguished from FFRWs with great confidence. This is shown in the flow diagram of FIG. 5D, which is carried out by the microprocessor, e.g., block 108 of FIG. 4. At 150, it is determined whether SIGmin is less than $K_0$. If yes, at 151 the flag is set equal to 1, meaning that the analysis of the SIG signal alone suggests a P wave. If no, at 152 the flag is set equal to 0, corresponding to an initial analysis of an FFRW. At 154, the SL signal is compared to the SL criteria; if SLmax is less than $K_1$, and SLmin is greater than $K_2$, then at block 155 the signal is classified as a P wave. However, if the answer at 154 is no, the routine goes to 156 and inspects the flag to recall the outcome of the SIG analysis. If the flag is set to 0, then both the SIG and SL signals indicate an FFRW, and at 157 the signal is classified is an FFRW. However, if the flag had been set to 1, the result is ambiguous, and at 158 it is determined that there is no event classification.

Figure 6:
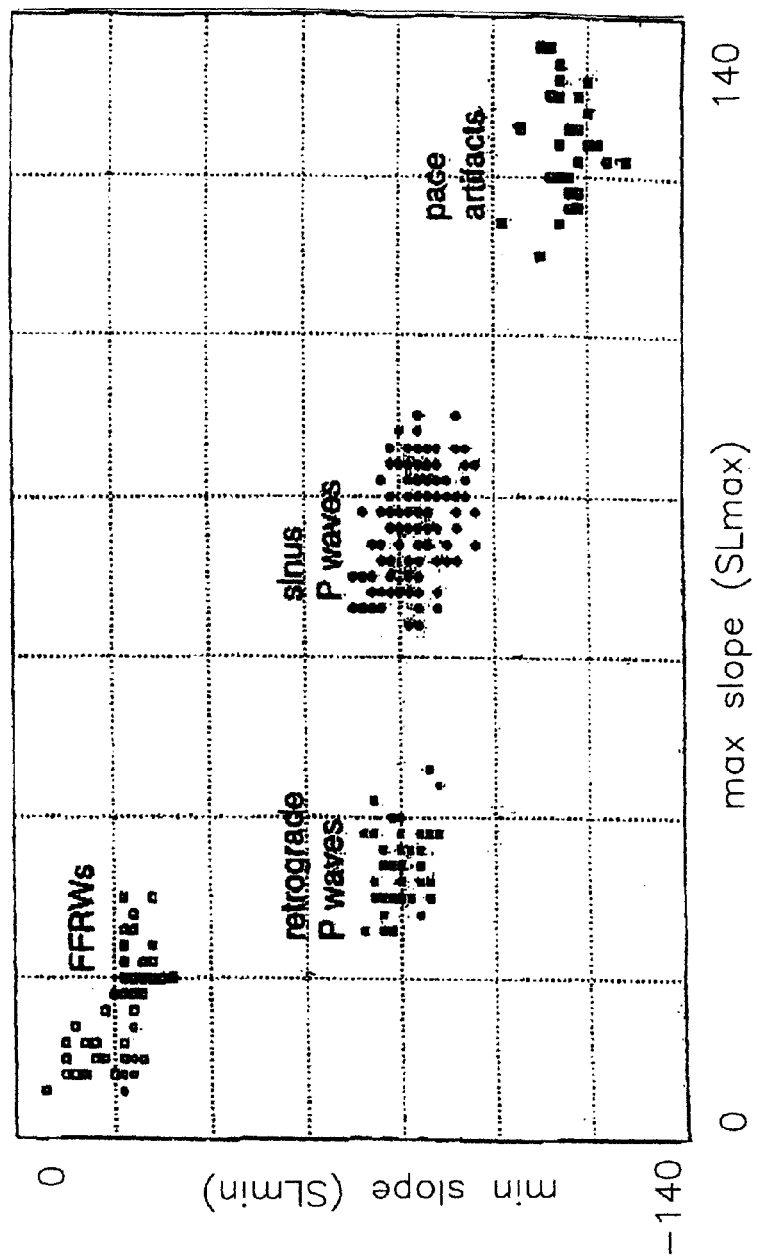
FIG. 6 is a plot of data representing slope minima and maxima, illustrating criteria for classifying atrial signals as FFRWs, retrograde P waves, sinus P waves and pace artifacts.

Referring now to FIG. 6, there is shown data relating to the SL signal, suggesting criteria for distinguishing FFRWs, retrograde P waves, sinus P waves and pace artifacts. Thus, if the magnitude of SLmin is less than 40, and SLmax is less than about 40, this data suggests classification as an FFRW. If the magnitude of SLmin is greater than 60 and SLmax is greater than 20 but less than 60, the signal appears to be a retrograde P wave. If the signal has an SLmin magnitude greater than 60 and less than 100; and an SLmax value greater than 60 but less than 100, it is suggested to be a normal or sinus P wave. And, if the SLmax value is greater than 100 the signal is suggested to be classified as a pace artifact. Thus, for a more sophisticated classification algorithm than that of FIG. 5D, these criteria can be incorporated. Also, although not shown in FIG. 6, PACs commonly have slope parameters different from normal sinus P waves, such that they can be distinguished by processing of a selected combination of the nine available parameters.

Figures 7A, 7B:
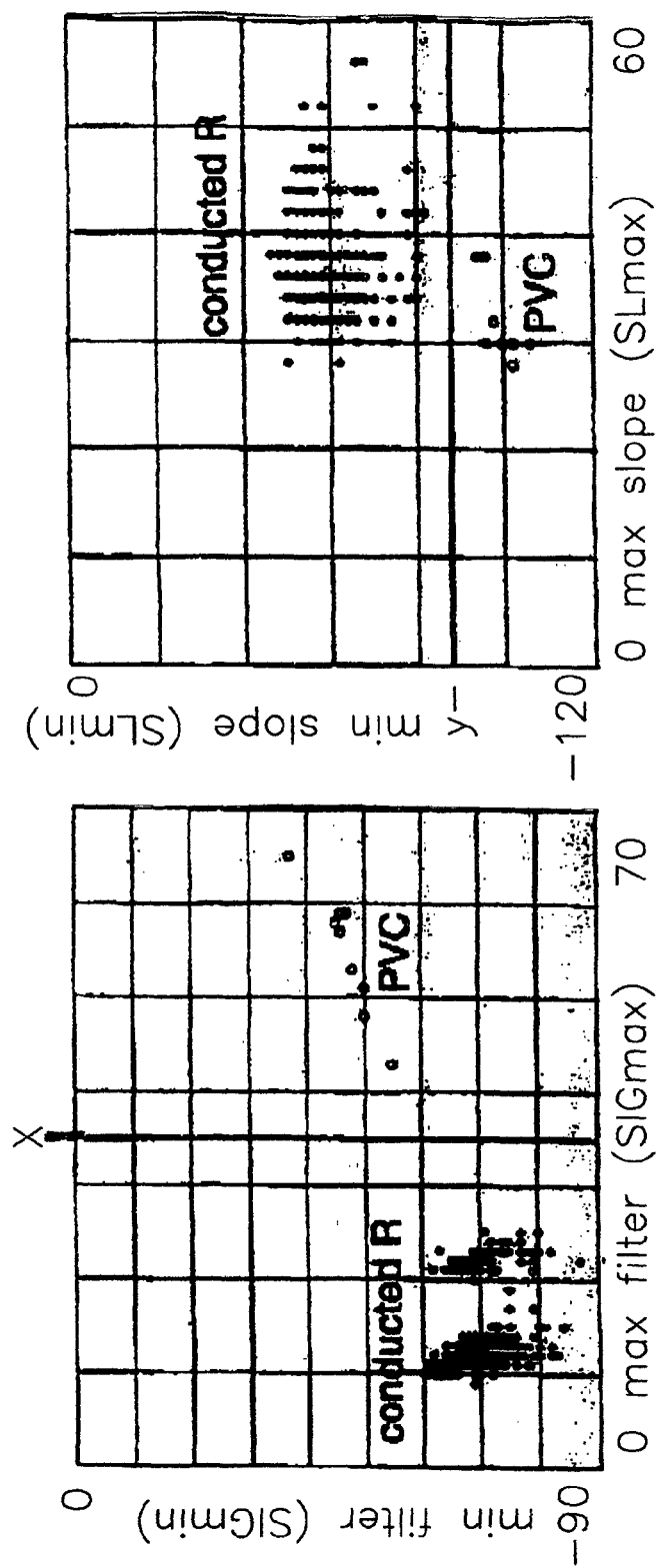
FIG. 7A is a plot of filtered signal data from a ventricle, illustrating criteria for distinguishing PVCs from normal conducted R waves.
FIG. 7B is a plot of slope data from the ventricle, illustrating differences of PVCs and normal conducted R waves.
Figure 7C:
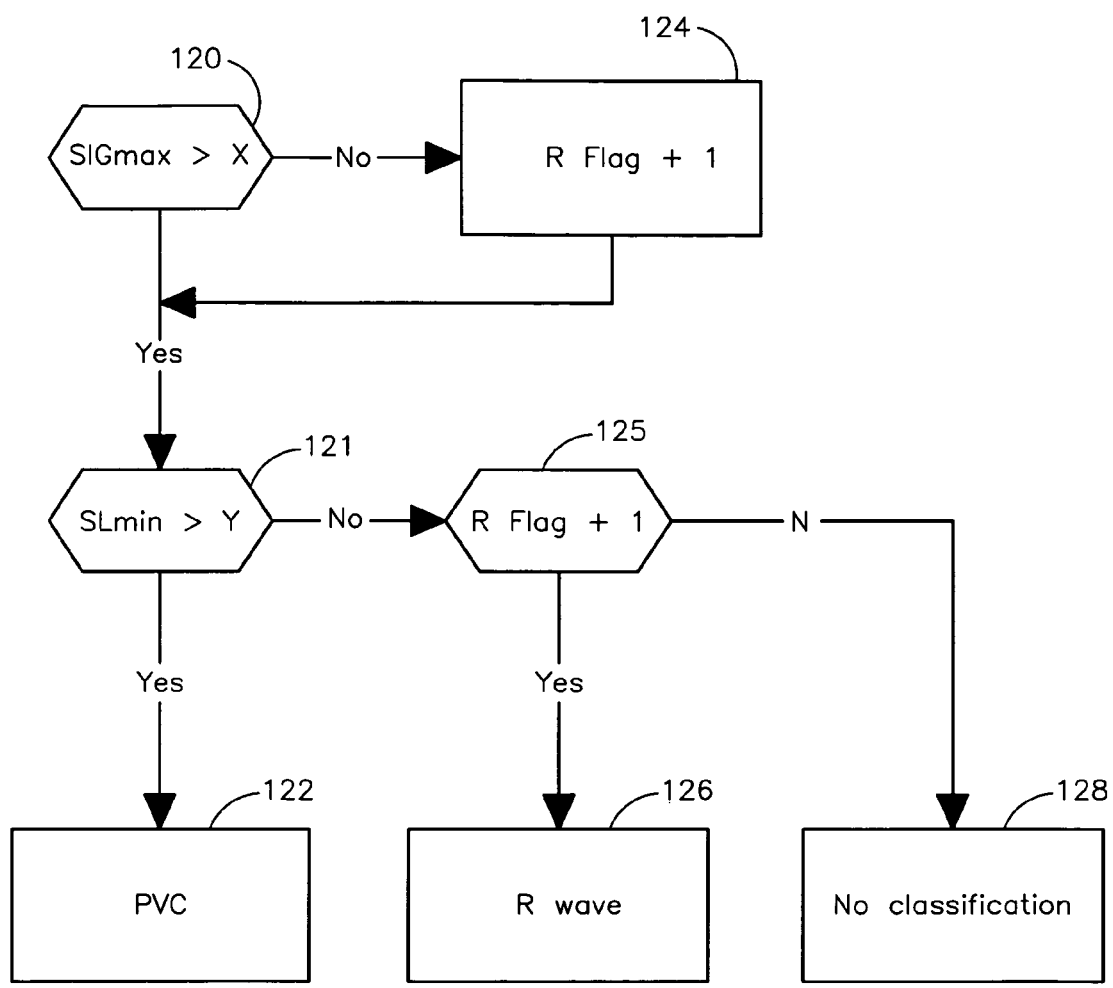
FIG. 7C is a flow diagram illustrating an algorithm for distinguishing PVCs from conducted R waves based upon criteria suggested by the above data.

Referring now to FIGS. 7A, 7B, 7C, there is illustrated the use of the invention for distinguishing PVCs from normal conducted R waves. FIG. 7A illustrates ventricular signal data, plotting SIGmin against SIGmax, while FIG. 7B plots SLmin against SLmax. FIGS. 7A and 7B suggest criteria for distinguishing a PVC from a conducted R wave, which criteria are utilized in the algorithm of FIG. 7C. As seen at block 120 and FIG. 7A, if SIGmax is greater than a constant X, this suggests the probability of the a PVC. If the comparison is positive, the routine goes to block 121 and compares the value of SLmin with the constant Y. As seen in FIG. 7B, if SLmin is greater than Y, this again suggests a PVC, and the routine goes to block 122 and classifies the event as a PVC. Returning to 120, if SIGmax is less than X, the routine goes to block 124 and sets the R flag=1. Then, if at 121 SLmin is found to be less than Y, the routine goes to block 125. If the R flag is already set to 1, this means that both criteria for an R wave are present, and the routine goes to block 126 and classifies the signal as an R wave. If the answer at 125 is no, at 128 the algorithm concludes that the situation is ambiguous, and there is no classification.

Figure 8A:
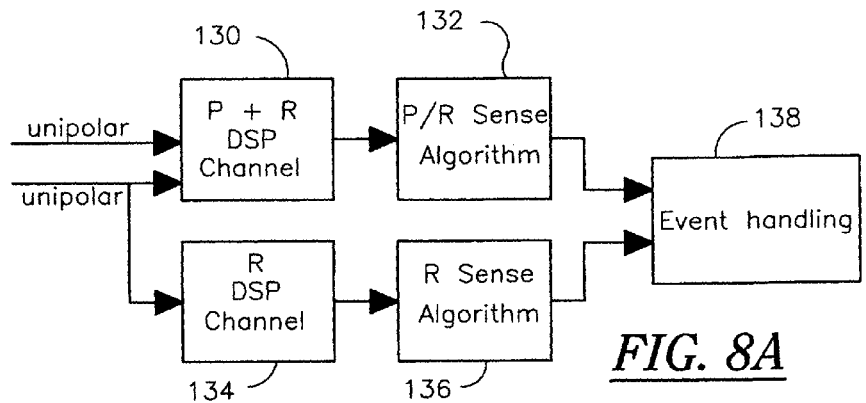
FIG. 8A is a block diagram illustrating a pacemaker in accordance with this invention utilizing combipolar sensing.
Figure 8B:
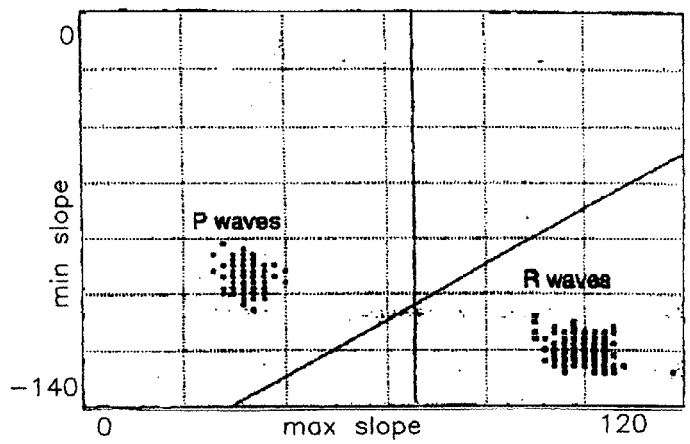
FIG. 8B is a plot illustrating slope data derived from combipolar signals.
Figure 8C:
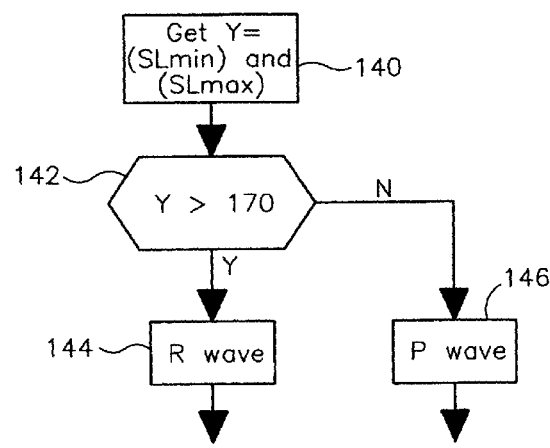
FIG. 8C is a simplified flow diagram illustrating an algorithm for distinguishing combipolar signals in terms of P waves and R waves.

Referring now to FIGS. 8A, B and C, there is illustrated the use of the combined DSP and software techniques of this invention with combipolar pacemaker sensing. As illustrated in FIG. 8A, this arrangement essentially provides bipolar differential sensing by means of an atrial unipolar lead and a ventricular unipolar lead. This arrangement is known to combine the advantages of bipolar sensing and unipolar leads, providing less interference by extraneous noise, and reduced sensing of myopotentials, FFRWs and other artifacts. The combined signals from the atrial and ventricular leads are inputted into channel block 130, designated P+R DSP channel. At the same time, the signal from the ventricular lead is inputted into the R DSP channel 134. The combined P+R sense and parameter signals are outputted from channel 130 and operated on by a P/R sense algorithm 132, which classifies the signal as a P wave or an R wave. Likewise, the sense and parameter signals from the R channel 134 are operated on by an R sense algorithm 136. Signals classified by either algorithm are sent for event handling. It is seen in FIG. 8B that P waves can be clearly demarcated from R waves by the diagonal line, which represents the sum of the magnitude of SLmin and SLmax. For this data, this sum is equal to 170, such that for any signal where the combined magnitude is less than 170, a P wave is indicated; whereas if the combined magnitudes are greater than 170, an R wave is indicated. As indicated at block 140 of FIG. 8C, in analyzing a sensed signal from the P+R channel, the algorithm first gets the sum of the magnitudes of the two slope parameters, at 140. At 142, it is determined whether this sum, indicated as Y, is greater than 170. If yes, the signal is classified as an R wave at 144; if no, it is classified as a P wave at 146. It is to be understood that while FIG. 8C presents logic steps limited to analyzing the slope parameters, the algorithm may additionally utilize any of the other parameters as shown in FIG. 3. Of course, where one parameter comparison, such as suggested by FIG. 8C, is seen to predict with a high confidence, it is weighted more than other comparisons. However, in general, one or more criteria can be combined on a logical AND or OR basis in the classification algorithm.

Figure 9A:
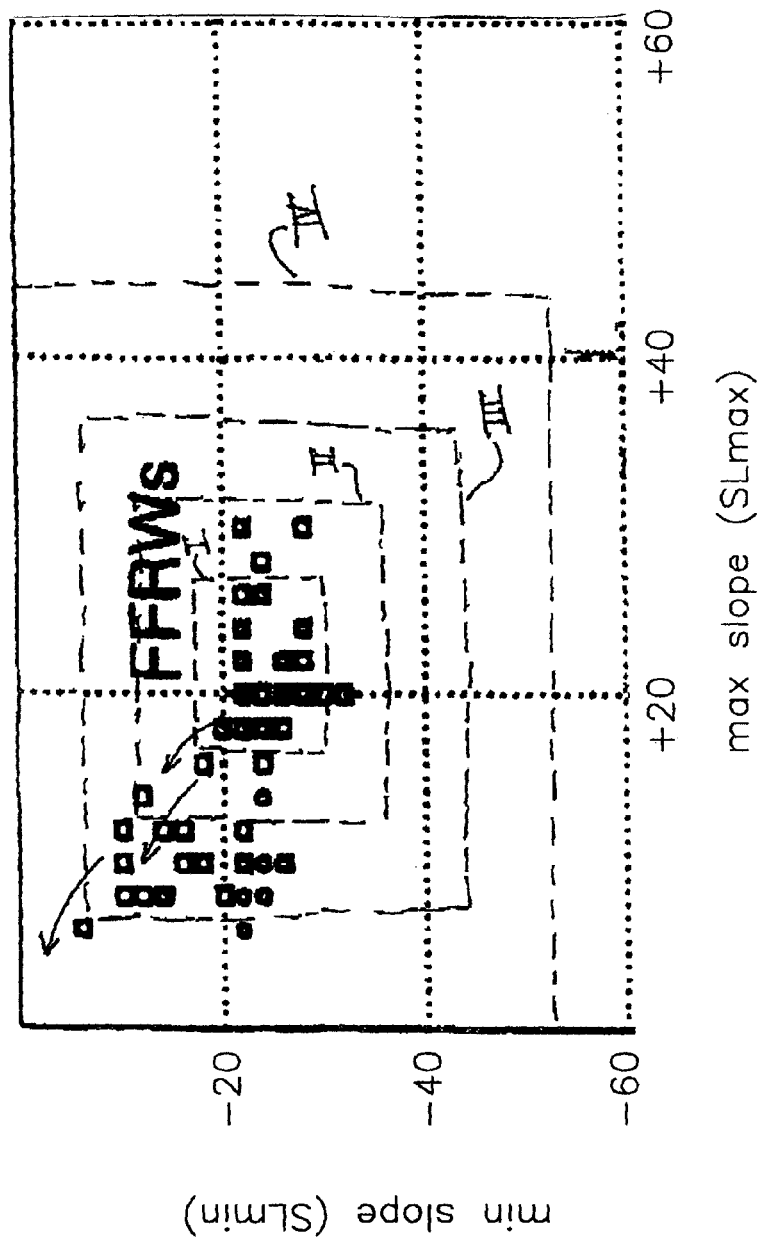
FIG. 9A shows an example graph of FFRW slope minima and slope maxima data used to detect changes in the heart condition of a patient in accordance with one embodiment of the present invention.
Figure 9B:
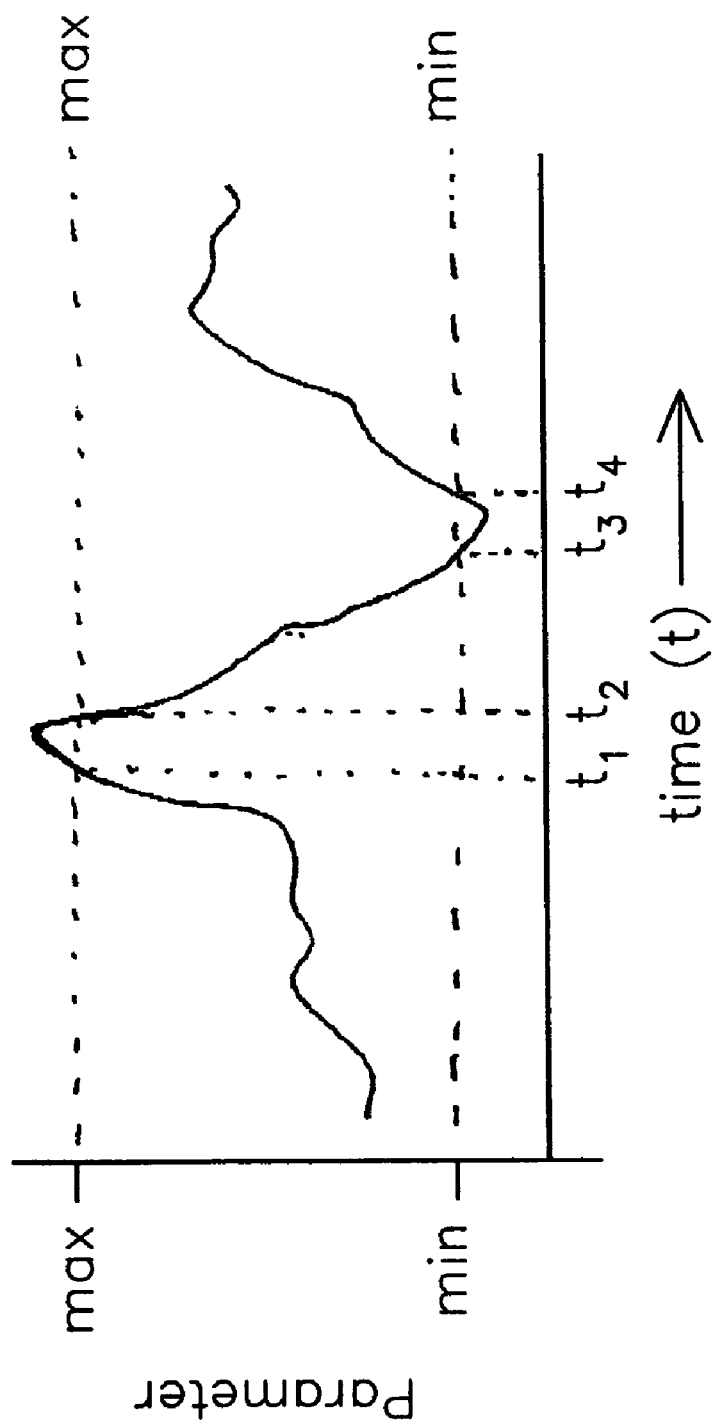
FIG. 9B shows a graph of the variation, over time, of wave parameter data, where the variation over a predetermined period or window of time of a monitored parameter or set of parameters corresponding to a particular type or classification of cardiac signal and derived in accordance with the one or more DSPs of the present invention is employed to detect the presence or onset of a predetermined heart condition such as ischemia or heart failure in accordance with one embodiment of the present invention.

Referring now to FIGS. 9A and 9B, there are shown further embodiments of the present invention where the variation, over time, of data or parameters associated with a particular type of intra-cardiac wave or event is continually monitored, determined and/or updated to aid in the detection of the onset or presence of a heart condition such as ischemia, heart failure or cardiomyopathy.

In accordance with such an embodiment of the present invention, the relevant monitored, detected, determined and/or updated change over time may be signal amplitudes, signal minima, signal maxima, signal magnitudes, signal slopes, signal widths, rates of change of any of the foregoing, combinations of any of the foregoing, wave parameters associated with any of the foregoing, and combinations of wave parameters associated with any of the foregoing. For example, when the monitored parameter corresponding to a particular type of cardiac wave or event exceeds, becomes equal or falls below a predetermined threshold, or when the monitored set of parameters corresponding to a particular type of cardiac wave or event changes characteristics in a predetermined fashion, or when the rate of change of any of the foregoing exceeds, becomes equal or falls below a predetermined threshold, or changes in a predetermined fashion, then the onset or development of ischemia, heart failure or cardiomyopathy may have been or is detected or indicated.

One example of such an embodiment of the present invention is now further described while continuing to refer to FIG. 9A. The characteristics of and wave parameters associated with intra-cardiac Far-Field R-Waves (FFRWs) have been discovered to change in some patients when the myocardium changes from being sufficiently or healthily oxygenated to being oxygen-deprived or ischemic, or from being less ischemic to more ischemic. More particularly, characteristics of intra-cardiac FFRWs wave parameters such as width, slope, amplitude and/or magnitude, and/or the rate of change of width, slope, amplitude, and/or magnitude have been discovered to change in some patients when the myocardium changes from being sufficiently or healthily oxygenated to being oxygen-deprived or ischemic, from being less ischemic to more ischemic, or from being less cardiomyopathic to more cardiomyopathic.

Furthermore, intra-cardiac IEGMs initially obtained in a patient known to have a non-ischemic or non-cardiomyopathic heart may be characterized in having FFRWs which, when subjected to the DSP steps of the present invention, result in SLmax vs. SLmin and/or SIGmax vs. SIGmin parameters which fall into a certain region of the min slope vs. max slope plots and/or min. filter (SIGmin) vs. max. filter (SIGmax) plots discussed in detail hereinabove.

By way of example and discussion, and continuing to refer to FIG. 9A, assume that a hypothetical patient having a sufficiently healthy oxygenated myocardium has been identified by a physician or appropriate software/hardware means constructed and employed in accordance with the teachings of the present invention as having FFRWs having min slope and max slope wave parameters corresponding to those falling within the dashed boundary lines of Region I shown in FIG. 9A. Assume further that the physician or software routine has further identified the area of FIG. 9 lying between the dashed lines marked "Region I" and "Region II" as a "buffer zone" where min slope and max slope wave parameters correspond to a condition of the myocardium which lies somewhere being sufficiently well oxygenated (i.e., Region I) and not being sufficiently well oxygenated (i.e., Regions III and IV, exclusive of Regions I and II). That is, data falling in Regions III and IV indicate an ischemic condition of the patient's myocardium. Assume further that the initial min slope/max slope FFRW data points acquired, sensed and calculated in accordance with the present invention fall within Region I.

Continuing to refer to FIG. 9A, over time the acquired and sensed FFRW waves and their associated wave parameters gradually move first into Region II and then into Regions III or IV. The change of region into which the FFRW wave parameters fall may be employed to trigger a warning, storage of acquired and/or sensed IEGM data, or the delivery of a therapy, more about which we say below. The fact that a wave parameter or a sequence of wave parameters meeting certain predetermined criteria fall into a particular area or portion of a graph may be employed to trigger such warnings, data storage or therapy delivery. The time rate at which the characteristics of wave parameters change may also be employed to trigger such warnings, data storage or therapy delivery. For example, the more quickly the change in a wave parameter associated with a particular type of cardiac event occurs, the sooner may the warning, data storage or therapy delivery be triggered.

It is generally preferred that a physician determine the appropriate boundaries and rates of change of the FFRW wave parameter regions which correspond to non-ischemic and ischemic conditions, or non-cardiomyopathic and cardiomyopathic conditions, in a particular patient. Alternatively, a software program may be stored in the memory of the microprocessor or DSP of the present invention to compare the FFRW parameters of the patient to those set forth in stored FFRW parameter data tables representative of typical healthy non-ischemic or non-cardiomyopathic patient populations, to thereby determine whether or not a patient's particular FFRW parameter data fall within the "healthy" region. To reduce the effects of spurious measurements or noise, a running average or median filtered version of such FFRW parameters may be continuously maintained or updated in the microprocessor, memory and/or DSP of the present invention.

It is also contemplated in the present invention that only one parameter of a given type of cardiac wave or event (such as the min slope of FFRWs) be monitored as a function of time for purposes of detecting the onset or development of an undesired cardiac condition such as ischemia, cardiomyopathy, and/or heart failure. Such an embodiment of the present invention is illustrated in FIG. 9B, where maximum and minimum thresholds for a given wave parameter set the upper and lower limits corresponding to a healthy heart in a given patient. Those thresholds may be determined by a physician, with the aid of the aforementioned look-up table technique, or through the use other suitable techniques. When the wave parameter being monitored as a function of time becomes equal to or exceeds the maximum threshold "max," then the presence of an unhealthy heart condition may be indicated in a particular patient. Contrariwise, when the wave parameter being monitored as a function of time becomes equal to or falls below the minimum threshold "min," then the presence of an unhealthy heart condition may also be indicated in a particular patient.

In accordance with various embodiments of the present invention, and regardless of whether one, two or more parameters associated with a given type of cardiac wave are being monitored, once the boundaries of the acceptable region corresponding to the given wave type have been crossed or the acceptable thresholds of such a wave type have been exceeded or fallen below, a device of the present invention may be triggered to perform one or more of the following functions: (a) alert a patient and/or physician audibly or otherwise of the patient's detected change in cardiac function or condition; (b) telemetrically communicate the patient's change in condition or function to a nearby external communication device, programmer or computer, which may then be further pre-programmed to telephonically, by internet means, or otherwise alert a hospital, physician or emergency medical service of the patient's detected change in cardiac function or condition; (c) provide an appropriate cardiac pacing therapy such as anti-tachycardia pacing to correct the condition; (d) provide an appropriate cardiac defibrillation therapy to correct the condition; (e) provide an appropriate cardioversion therapy to correct the condition; (e) dispense a predetermined amount of a drug or gene therapy into the patient's bloodstream or cardiac tissue by means of an implantable drug pump forming a part of, attached to or in communication with the pacing or defibrillation device or its associated electrical stimulation and/or sensing leads; or (g) capture detailed diagnostic data over a predetermined time period for subsequent processing and analysis.

Note that in the present invention the wave type being considered in diagnosing or detecting a change in cardiac function or condition is not limited to FFRWs or to cardiac events sensed in the atrium. Indeed, many other types of intracardiac waves may be classified in accordance with the teachings of the present invention, and may also be continuously monitored in a manner similar to that outlined above respecting FFRWs to detect a change in cardiac condition or function. The maximum or minimum slope, width, maximum or minimum amplitude, and/or maximum or minimum magnitude of R waves, evoked response R waves, QT waves, and/or portions of QT waves corresponding to depressed QT waves, may all be employed in one fashion or another in accordance with the teachings of the present invention to detect ischemia, for example. Measured QT wave times and T wave polarity changes may be similarly employed in still other embodiments of the present invention.

In one embodiment of the present invention, cardiac events originating in the left or right ventricles may be sensed using an appropriate ventricular lead, and then amplified, filtered and classified in accordance with the teachings of the present invention as R waves, evoked R waves, T waves, evoked T waves, Q waves, evoked Q waves, ventricular tachycardia, ventricular flutter, re-entrant ventricular tachycardia, and supraventricular tachycardia.

For example, and in still another embodiment of the present invention, R waves or evoked response R waves acquired or sensed in one or more ventricles of the heart are employed to detect the onset, development or presence of ischemia, cardiomyopathy and/or heart failure. The slope and/or width of those R waves or evoked response R waves, or the change in the slope and/or width of those R waves or evoked response R waves, may be of particular interest in assessing whether or not an ischemic condition exists or is at risk of developing in a patient's myocardium. This is because the conduction velocity at which an R wave or evoked response R wave propagates through the myocardium may change upon the onset, development or presence of ischemia, cardiomyopathy and/or heart failure, typically by such conduction velocity becoming slower and the width W of the R wave or evoked response R wave increasing. According to the particular patient at hand, however, such a conduction velocity may increase or decrease, the amplitude of the R wave or evoked response R wave may become larger or smaller, or the width of the R wave or evoked response R wave may become greater or lesser. Thus, in accordance with most embodiments of the present invention where a patient's cardiac function or condition are to be continuously monitored, it is preferable to obtain one or a series of IEGMs from the patient when the condition to be detected, for example ischemia or cardiomyopathy, is not present, or when the function to be monitored, for example the generation in the ventricle of normal R waves or evoked response R waves, is normal.

Figure 10:
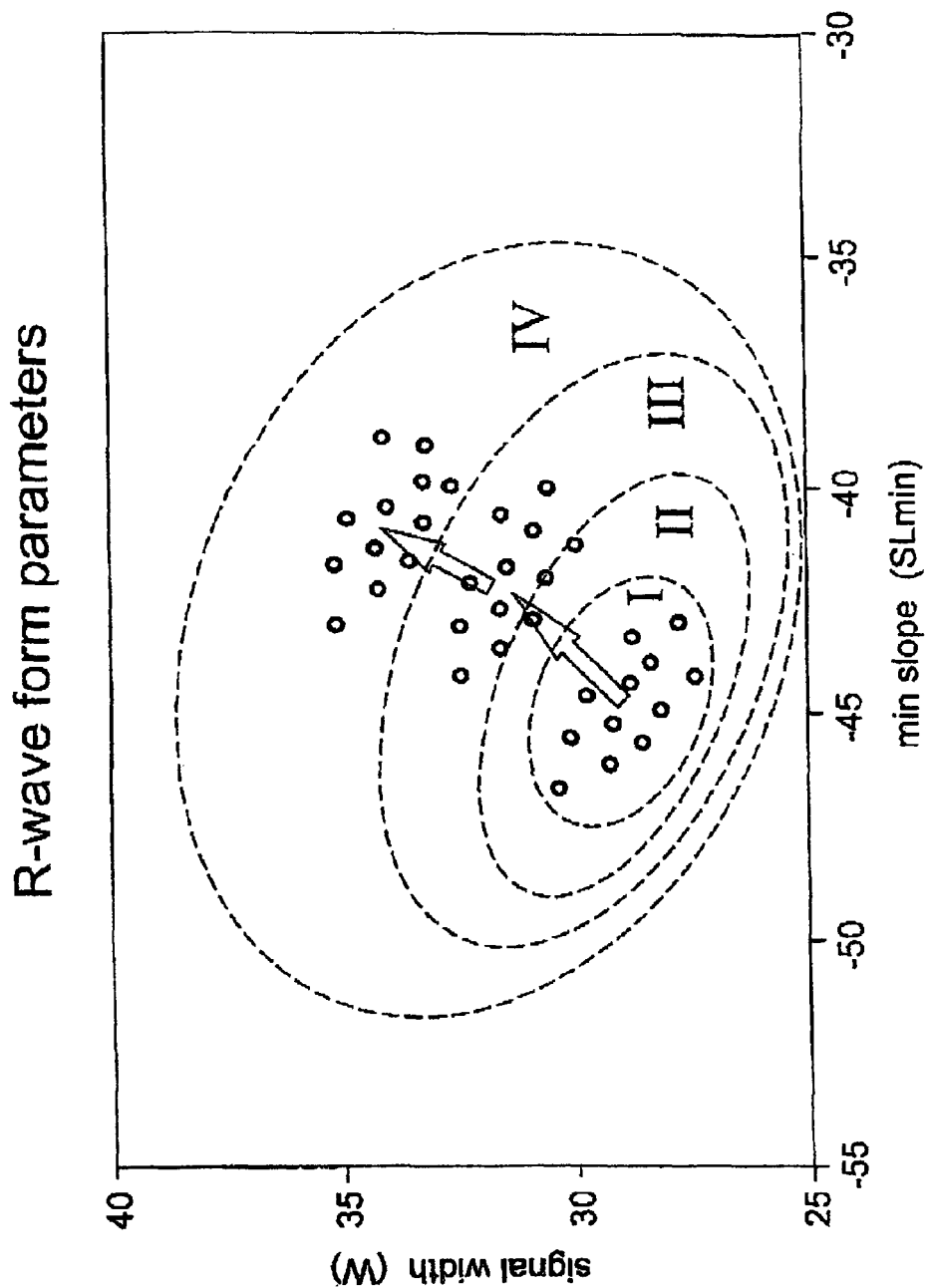
FIG. 10 shows a graph of the variation, over time, of R wave parameter data, where the variation over a predetermined period or window of time of R wave SLmin and W parameters derived in accordance with the one or more DSPs of the present invention is employed to detect the presence or onset of a predetermined heart condition such as ischemia or cardiomyopathy in accordance with another embodiment of the present invention.

Referring now to FIG. 10, there is shown a graph of the variation, over time, of R wave width and min slope parameter data, where the variation over a predetermined period or window of time of R wave SLmin and W parameters derived in accordance with the one or more DSPs of the present invention is employed to detect the presence or onset of a predetermined heart condition such as ischemia or cardiomyopathy.

By way of example and discussion, and continuing to refer to FIG. 10, assume that a hypothetical patient having a sufficiently healthy oxygenated myocardium has been identified by a physician or appropriate software/hardware means constructed and employed in accordance with the teachings of the present invention as having R waves or evoked response R waves having signal width (W) and min slope (SLmin) wave parameters corresponding to those falling within the dashed boundary lines of Region I shown in FIG. 10. Assume further that the physician or software routine has further identified the area of FIG. 10 lying between the dashed lines marked "Region I" and "Region II" as a "buffer zone" where W and SLmin wave parameters correspond to a condition of the myocardium which lies somewhere being sufficiently well oxygenated (i.e., Region I) and not being sufficiently well oxygenated (i.e., Regions III and IV, exclusive of Regions I and II). That is, data falling in Regions III and IV indicate an ischemic or cardiomyopathic condition. Assume further that initial W and SLmin R wave data points acquired, sensed and calculated in accordance with the present invention fall into Region I.

Continuing to refer to FIG. 10, over time the acquired and/or sensed R waves and their associated wave parameters gradually move first into Region II and then into Regions III or IV. The change of region into which the R wave parameters fall or the time rate at which certain characteristics of those parameters change may be employed to trigger a warning, storage of acquired and/or sensed IEGM data, or the delivery of a therapy in a fashion similar to that described above in respect of FFRW waves.

It is generally preferred that a physician determine the appropriate boundaries and rates of change of the R wave or evoked response R wave parameter regions which correspond to non-ischemic and ischemic conditions, or non-cardiomyopathic and cardiomyopathic conditions, in a particular patient. Alternatively, a software program may be stored in the memory of the microprocessor or DSP of the present invention to compare the R wave or evoked response R wave parameters of the patient to those set forth in stored R wave or evoked response R wave parameter data tables representative of typical healthy non-ischemic or non-cardiomyopathic patient populations, to thereby determine whether or not a patient's particular R wave or evoked response R wave parameter data fall within the "healthy" region. To reduce the effects of spurious measurements or noise, a running average or median filtered version of such R wave parameters may be continuously maintained or updated in the microprocessor, memory and/or DSP of the present invention.

It is also contemplated in the present invention that only one parameter of a given type of cardiac wave or event (such as the width of R waves or evoked response R waves) be monitored as a function of time for purposes of detecting the onset or development of an undesired cardiac condition such as ischemia, cardiomyopathy, and/or heart failure.

It is further contemplated in the present invention that sets of wave parameter data may be subjected to two- or three-dimensional digital filtering routines as a further means of detecting the onset, development or presence of an undesired heart condition in a patient. For example, sets of R wave and/or evoked response R wave width (W) and min slope (SLmin) data may be three-dimensionally filtered in respect of signal width, signal minimum slope and time to yield an instantaneous measure of the condition of a patient's heart. Width and minimum slope R wave parameter data which change at a rate exceeding a predetermined minimum rate of change, for example, might be flagged using such a three-dimensional filter to provoke the provision of a warning, delivery of a pacing or defibrillation therapy, or delivery of a drug or gene therapy.

Those skilled in the art will recognize that signals may be processed according to the present invention using computing devices such as digital signal processors, microprocessors, Application Specific Integrated Circuits ("ASICs"), controllers, micro-controllers, mini-controllers, computers, micro-computers, mini-computers, Central Processing Units (CPUs), and the like.

The preceding specific embodiments are illustrative of the practice of the invention. It is to be understood, therefore, that other expedients known to those skilled in the art or disclosed herein may be employed without departing from the invention or the scope of the appended claims.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination.

All printed publications and patents referenced hereinabove are hereby incorporated by referenced herein, each in its respective entirety.

We claim:

1. A cardiac pacing system having a pacemaker and lead means for inter-connecting the pacemaker and the patient's heart, the pacemaker having pulse means for generating pacing pulses and control means for controlling the operation of the pacemaker, the lead means having electrode means for delivering pacing pulses to a patient's heart and for acquiring cardiac signals, the pacemaker having DSP means for amplifying and processing the cardiac signals acquired by the electrode means, and means for classifying the acquired cardiac signals, the DSP means comprising at least one DSP channel, the pacing system comprising:

conversion means for converting the acquired and amplified signals to digital signals;

digital filter means for filtering the converted signals to provide filtered signals;

slope means for operating on the filtered signals to provide slope signals representative of the slope of the filtered signals;

sense means for determining from the filtered signals and the slope signals whenever a cardiac event is detected, and the sense time of each detection;

analysis window means for timing out an analysis window of predetermined duration following the sense time;

parameter means for processing the filtered signals and the slope signals during the analysis window, and for generating a plurality of respective parameters from the signals;

classification means for receiving the parameters from the DSP means and for classifying each signal as a function of the parameters, and monitoring means for determining and detecting whether each classified signal corresponds to a predetermined heart condition.

2. The system described in claim 1, wherein the pacemaker comprises a computing device selected form the group consisting of a Digital Signal Processor ("DSP"), a microprocessor, an Application Specific Integrated Circuits ("ASIC"), a controller, a micro-controller, a mini-controller, a computer, a micro-computer, and a Central Processing Unit (CPU), and the classification means comprises the computing device and an algorithm for operating upon the parameters.

3. The system described in claim 2, wherein the electrode means comprises means for acquiring a plurality of respective intracardiac signals, and wherein the DSP means comprises a plurality of the channels, each channel corresponding to a respective one of the intracardiac signals, and wherein the classification means comprises a plurality of respective programmable algorithms for processing the parameters generated by each the channel.

4. The system described in claim 1, wherein the conversion means comprises a delta-sigma modulator circuit, and wherein DSP means further comprises interconnection means for interconnecting the conversion means, the digital filter means, the slope means, the sense means and the parameter means.

5. The system described in claim 1, wherein the parameter means comprises means for deriving four parameters from the filtered signal during each the analysis window and for deriving four respective parameters from the slope signal during each the analysis window, and wherein the classification means comprises means for classifying each acquired signal as a function of the four signal parameters and the four slope parameters.

6. The system described in claim 5, wherein the parameter means further comprises means for deriving a signal length as a function of comparing the filtered signals and the slope signals to predetermined threshold criteria.

7. The system described in claim 1, wherein the sense means comprises means for comparing the filtered signals with at least one predetermined threshold and for comparing the slope signals with at least another predetermined threshold.

8. The system described in claim 7, wherein the sense means comprises means for determining when the magnitude of the filtered signals has exceeded the one predetermined threshold and the magnitude of the slope signals has exceed the another threshold within a predetermined time interval.

9. The system described in claim 1, wherein the parameter means comprises means operative during the analysis window for determining a minimum and maximum value for the filtered signals and for the slope signals.

10. The system described in claim 9, wherein the electrode means comprises means for acquiring atrial signals, and the classifying means comprises means for distinguishing at least one of P waves, R waves and FFRWs as a function of the minimum and maximum values for the filtered signals.

11. The system described in claim 10, wherein the classifying means comprises means for distinguishing P waves and FFRW waves as a function of the sum of the slope maximum and minimum absolute values during the analysis window.

12. The system described in claim 10, wherein the classifying means comprises stored criteria relating to retrograde P waves, and comprises a software algorithm for distinguishing retrograde P waves from natural sinus P waves by comparing the minimum and maximum values to the criteria.

13. The system described in claim 10, wherein the classifying means comprises means for distinguishing at least two of FFRWs, intrinsic P waves, evoked response P waves, retrograde P waves, PACs, sinus P waves, evoked response R waves, and R waves from one another.

14. The system described in claim 9, wherein the electrode means comprises means for acquiring ventricular signals, and wherein the classifying means comprises means for classifying PVCs.

15. The system described in claim 1, further comprising means for triggering a predetermined response by the pacemaker system in response to detection of the predetermined heart condition.

16. The system described in claim 15, wherein the means for triggering a predetermined response is operably connected to a means for delivering the predetermined response.

17. The system as described in claim 16, wherein the means for delivering the predetermined response is selected from the group consisting of an intracardiac drug therapy localized delivery apparatus, at least one intracardiac pacing electrode, at least one intracardiac defibrillation electrode, and an intracardiac gene therapy localized delivery apparatus.

18. The system described in claim 1, wherein the predetermined heart condition is ischemia or cardiomyopathy and the monitoring and detecting means further comprises means for distinguishing between FFRWs or R waves corresponding to an ischemic or cardiomyopathic condition of the patient's heart and FFRWs or R waves corresponding to a non-ischemic or non-cardiomyopathic condition of the patient's heart.

19. The system as described in claim 1, wherein the monitoring and detecting means further comprises means for differentiating between classified signals on the basis of wave parameters.

20. The system as described in claim 19, wherein the wave parameter employed by the differentiating means is selected from the group consisting of positive signal slope, negative signal slope, positive signal amplitude, negative signal amplitude, delay times corresponding to maximum values of signals, delay times corresponding to minimum values of signals, and any combination of the foregoing.

21. A method of detecting a heart condition in a patient's heart using a cardiac pacing system, the cardiac pacing system having a pacemaker and lead means for inter-connecting the pacemaker and the patient's heart, the pacemaker having pulse means for generating pacing pulses and control means for controlling the operation of the pacemaker, the lead means having electrode means for delivering pacing pulses to a patient's heart and for acquiring cardiac signals, the pacemaker having DSP means for amplifying and processing the cardiac signals acquired by the electrode means, and classifying means for classifying acquired cardiac signals, the DSP means comprising at least one DSP channel, the pacing system comprising conversion means for converting the acquired and amplified signals to digital signals, digital filter means for filtering the converted signals to provide filtered signals, slope means for operating on the filtered signals to provide slope signals representative of the slope of the filtered signals, sense means for determining from the filtered signals and the slope signals whenever a cardiac event is detected, and the sense time of each the detection, analysis window means for timing out an analysis window of predetermined duration following the sense time, parameter means for processing the filtered signals and the slope signals during the analysis window, and for generating a plurality of respective parameters from the signals, classification means for receiving the parameters from the DSP means and for classifying each signal as a function of the parameters, and monitoring means for determining whether each classified signal corresponds to a predetermined heart condition, the method comprising:

(a) acquiring an intracardiac signal;
(b) amplifying the acquired intracardiac signal;
(c) filtering the amplified intracardiac signal to provide a filtered signal;
(d) operating on the filtered signal to a provide a slope signal;
(e) determining from the filtered signal and slope signal when a cardiac event has been detected;
(f) processing the filtered signal and the slope signal during an analysis window triggered by the detection of a cardiac event;
(g) generating wave parameters corresponding to each of the filtered signal and the slope signal;
(h) classifying each signal as a function of the wave parameters;
(i) determining and detecting on the basis of the wave parameters whether each classified signal corresponds to a predetermined heart condition.

22. The method of claim 21, further comprising triggering a predetermined response by the pacemaker system when the predetermined heart condition is detected.

23. The method of claim 22, wherein the predetermined response is selected from the group consisting of delivering a drug, delivering a gene therapy, delivering a pacing therapy, delivering a defibrillation therapy, delivering a cardioversion therapy, and delivering an anti-tachycardia pacing therapy.

24. The method of claim 21, wherein the predetermined heart condition is ischemia or cardiomyopathy and the monitoring and detecting means further distinguishes between FFRWs, R waves or evoked response R waves corresponding to an ischemic or cardiomyopathic condition of the patient's heart and FFRWs, R waves or evoked response R waves corresponding to a non-ischemic or non-cardiomyopathic condition of the patient's heart.

25. The method of claim 21, further comprising acquiring and classifying at least one intracardiac control signal corresponding to a healthy cardiac condition of the patient.

26. The method of claim 25, further comprising storing in a memory of the system at least one control wave parameter corresponding to the at least one control signal.

27. The method of claim 26, further comprising comparing the at least one control wave parameter to a wave parameter corresponding to an acquired signal.

28. The method of claim 27, further comprising determining, on the basis of the comparison between the control signal wave parameter and the acquired signal wave parameter, whether the predetermined heart condition exists.

29. The method of claim 21, further comprising differentiating between classified signals on the basis of wave parameters.

30. The method of claim 29, wherein the wave parameter employed in differentiating is selected from the group consisting of positive signal slope, negative signal slope, positive signal amplitude, negative signal amplitude, delay times corresponding to maximum values of signals, delay times corresponding to minimum values of signals, signal width, and any combination of the foregoing.

31. The method of claim 21, further comprising storing in a memory of the system a plurality of wave parameters corresponding to a plurality of sensed cardiac events.

32. The method of claim 21, further comprising detecting changes in the characteristics of the plurality of stored wave parameters as new wave parameters are stored in the memory.

33. The method of claim 21, wherein only one wave parameter is employed to detect the predetermined heart condition.

34. The method of claim 21, wherein both wave parameters are employed to detect the predetermined heart condition.

* * * * *